United States Patent [19]

McMurray

[11] Patent Number: 5,126,348
[45] Date of Patent: Jun. 30, 1992

[54] BIOAVAILABILITY ENHANCERS

[75] Inventor: William H. McMurray, Firestone, Colo.

[73] Assignee: The University of Colorado Foundation, Inc., Boulder, Colo.

[21] Appl. No.: 412,795

[22] Filed: Sep. 26, 1989

[51] Int. Cl.$^5$ .................. A61K 31/44; A61K 31/52
[52] U.S. Cl. .................................... 514/264; 514/356
[58] Field of Search ......................... 514/356, 264

[56] References Cited

PUBLICATIONS

EPO Publication 106,335, published Apr. 25, 1984.
Ther. L. and Winne, D., (1971), "Drug Absorption", pp. 57-69.
Cadwallader, D. E., (1971), Biopharmaceutics and Drug Interactions, (Roche Laboratories, Nutley, N.J.), p. 53.
Cadwallader, D. E., (1971), Biopharmaceutics and Drug Interactions, (Roche Laboratories, Nutley, N.J.), p. 108.
McLean, A. J., (1978), Clin. Pharmacol. Ther., 24:5-10.
Schneck, D. W. and Vary, J. E., (1984), Clin. Pharmacol. Ther., 35:447-453.
Condorelli, L., (1964), in Niacin in Vascular Disorders and Hyperlipemia, R. Altschul (ed.), pp. 162-164. (See Ref. O).
Svedmyr, N. et al., (1970), in Metabolic Effects of Nicotinic Acid and its Derivatives, K. F. Gey and L. A. Carlson (eds.), Hans Huber Pub., pp. 1085-1098.
Grigoleit, H.-G. et al., (1976), Therapiewoche, 26:5722-5729.
Lindberg, N.-O., (1970), Acta Pharm. Svecica. 7:23-28.
Waller, A. R., (1985), Arnzeim.-Forsch./Drug Res., 35:489-492.
Mosher, L. R., (1970), Am. J. Psychiat., 126:1290-1296.
Abramson, D. I. et al., (1940), Am. J. Med. Sci., 200:96-102.
Popkin, R. J., (1939), Am. Heart J., 18:697-704.
Condorelli, L., (1964), in Niacin in Vascular Disorders and Hyperlipemia, R. Altschul (ed.), pp. 156-207.
Andersson, R. G. G. et al., (1977), Acta Pharmacol. et Toxicol., 41:1-10.
Svedmyr, N. et al., (1969), Clin. Pharmacol. Therapeut., 10:559-570.
Bechgaard, H. and Jespersen, S., (1977), J. Pharmaceut. Sci., 66:871-872.
Nickerson, M., (1975), The Pharmacological Basis of Therapeutics, Chapter 34, L. S. Goodman and A. Filman (eds.), pp. 745-760.
Stella, V. J. et al., (Feb. 1978), Kans. Pharmacy, pp. 12-13.
Levy, G., (1963), in Salicylates, an International Symp., Dixon et al. (eds.), pp. 9-17.
Koysooko et al., (1974), Clin. Pharmacol. Therapeut., 15:454-460.
Levy, G. et al., (1974), Pediatrics, 53:873-876.
Hendeles, L. et al., (1985), Chest, 88:103S-111S.
Piafsky, K. M. and Ogilvie, R. I., (1975), New Engl. J. Med., 292:1218-1222.
Brattsand, R. and Harthon, L., (1975), Acta Pharmacol. Toxicol., 36:203-214.
Cadwallader, D. E., (1971), Biopharmaceutics and Drug Interactions, (Roche Laboratories, Nutley, N.J.), p. 48.

*Primary Examiner*—S. J. Friedman
*Attorney, Agent, or Firm*—Greenlee and Winner

[57] ABSTRACT

Vasodilators and theophylline.

2 Claims, 1 Drawing Sheet

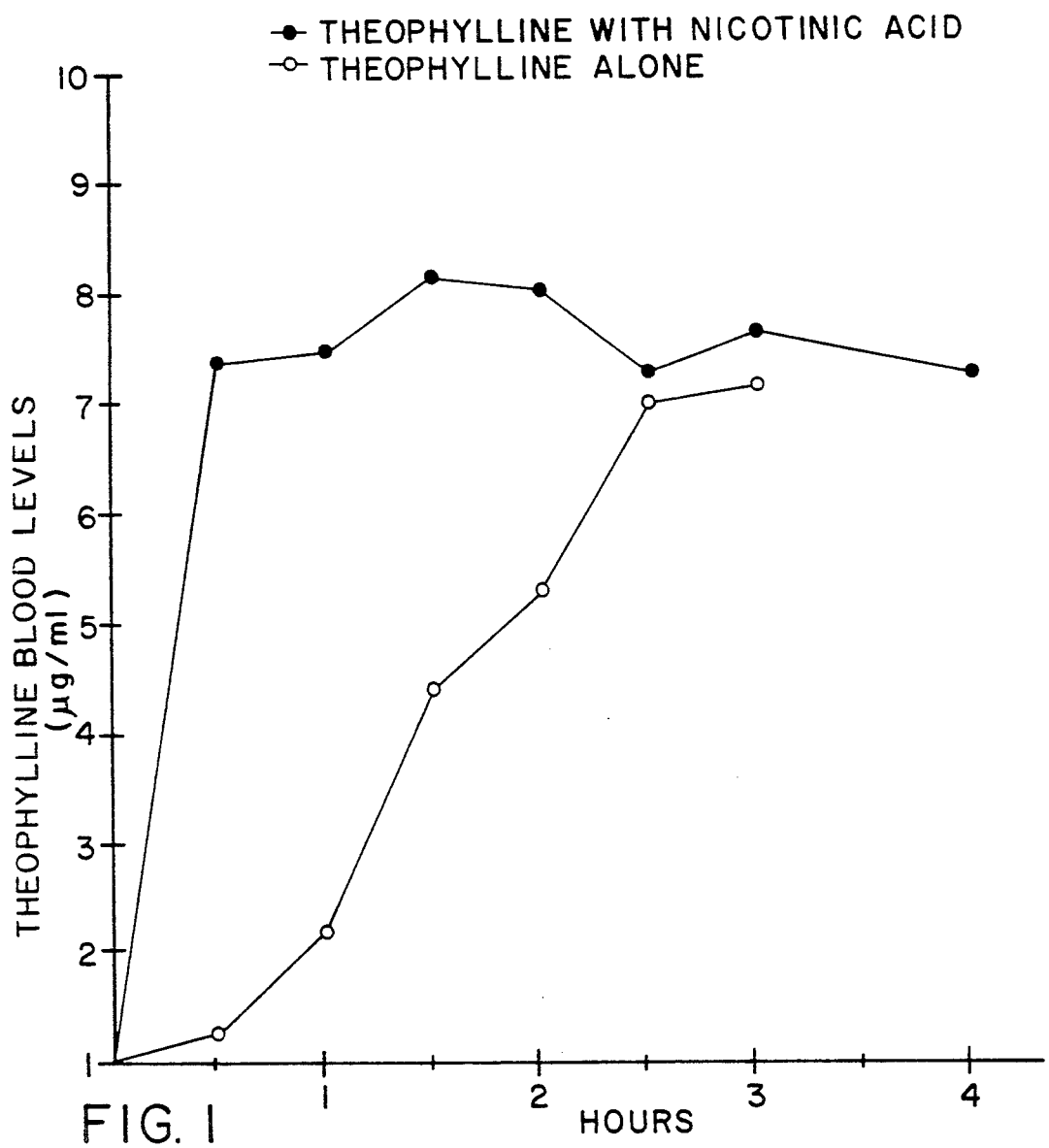

BIOAVAILABILITY ENHANCERS

FIELD OF THE INVENTION

This invention relates to pharmaceutical compositions comprising vasodilators, such as nicotinic acid (niacin), which affect the blood vessels of the gastrointestinal tract to enhance the bioavailability of the pharmaceutically active compounds present in said compositions.

BACKGROUND OF THE INVENTION

The use of vasodilators which affect the blood vessels of the gastrointestinal tract to enhance the bioavailability of pharmaceutically active compounds which are subject to passive diffusion absorption from the gastrointestinal tract has not been previously reported in the literature.

The concept of bioavailability is discussed, e.g., in R.D. Hossie et al. (June 1972), "Biopharmaceutical Evaluation of Drug Formulations, Can. Pharm. J. 27/189— 31/193.

Bioavailability is generally measured using drug-serum concentration-time curves, and includes such factors as rate of entry of the drug into the bloodstream, rate of achieving maximum concentration, and area under the curve. See, e.g., J. Koch Weser (1974), "Bioavailability of Drugs," New Engl. J. Med. 291:233-237. Many factors are known to affect bioavailability of drugs. Such factors include the nature of the form of the drug (ester, salt, complex, etc.); the physical state, particle size and surface area; presence or absence of adjuvants with the drug, type of dosage form in which the drug is administered; and pharmaceutical processes used to make the dosage form. See, e.g., D.E. Cadwallader, (1971) "Biopharmaceutics and Drug Interactions," (Roche Laboratories, Nutley, NJ).

Manipulations of many of these parameters have been reported in the literature as effective means for increasing drug absorption and bioavailability. For example, as regards the physical state of the drug, U.S. Pat. Nos. 4,088,750 and 4,002,718 report increasing bioavailability of digoxin by administering the drug in capsule form. U.S. Pat. No. 4,639,370 reports incorporating a biologically active substance into a water-swellable, water-insoluble polymer. U.S. Pat. Nos. 4,444,769, 4,526,777 and 4,547,498 report special granular formulations of active ingredients, particularly triamterene and hydrochlorothiazide. U.S. Pat. No. 4,562,181 reports an amorphous form of cefuroxime axetil with improved bioavailability. U.S. Pat. Nos. 4,725,429, 4,727,088 and 4,738,956 report a "stick" formulation of benzoyl peroxide for topical application. U.S. Pat. No. 4,758,427 reports the dispersion of psychoactive 2-aryl pyrazolo quinolines in polyvinylpyrrolidone to enhance absorption.

With respect to the use of adjuvants, U.S. Pat. No. 2,899,357 discloses the use of inactive bis-quaternary ammonium alkanes as adjuvants to tie up gastro-intestinal binding sites and allow greater bioavailability of active quaternary ammonium salts. U.S. Pat. No. 4,751,241 reports the use of polyglycerol esters of unsaturated fatty acids to enhance solubility of active drugs. U.S. Pat. No. 4,650,664 reports the use of acid salts of the drug and acid substances to enhance bioavailability of mopidamol. U.S. Pat. No. 4,427,648 reports the use of acid salts of the drug and acid substances to enhance bioavailability of dipyridamole. U.S. Pat. No. 4,731,360 reports the use of acylcarnitine to enhance absorption of beta-lactam antibiotics through mucous membranes. EPO Publication 119737 reports the use of cyclodextrin to enhance the bioavailability of a wide range of drugs. EPO Publication 035770 reports the use of a number of organic acids to enhance the bioavailability of glycosidic and related antibiotics. EPO Publication 192263 reports enhancing absorption of a benzoyl urea compound with cyclodextrin, polyethylene glycol or refined oil. U.S. Pat. No. 4,464,363 discloses certain aryl adjuvants as increasing the bioavailability of rectally administered insulin and other drugs. EPO Publication 65450 reports enhanced bioavailability of nifedipine with a beta-blocker. EPO Publication 164588 reports solid dihydropyridine formulations with good bioavailability containing a sparingly soluble dihydropyridine derivative with a readily water soluble filler. U.S. Pat. No. 4,704,405 reports the use of bases to enhance the bioavailability of Sulindac.

U.S Pat. No. 4,689,228 reports the use of complex carbohydrates to enhance absorption of calcium and other minerals.

Surfactants have also often been used to enhance bioavailability. U.S. Pat. No. 4,412,986 reports that nifedipine absorption is enhanced by compounding with a number of substances including surface active agents. U.S. Pat. No. 4,665,098 reports the enhancement of retinamide bioavailability using corn oil and a surfactant. U.S. Pat. No. 4,571,334 reports the use of a surfactant in the lung to enhance absorption of an anti-cancer drug. EPO Publication 031603 reports the use of surfactants to increase drug absorption, particularly 4-(monoalkylamino)benzoic acid and derivatives. U.S. Pat. No. 4,344,934 reports the use of water-soluble polymers and wetting agents to enhance solubility of drugs. EPO Publication 111841 reports the use of bile surfactants to enhance nasal absorption of LHRH agonists or antagonists. EPO Publication 292050 reports the use of surfactants to increase the bioavailability of flunarizine. EPO Publication 242643 reports the use of polysorbate-80 to decrease irritation caused by surfactant-drug preparations for nasal absorption.

The use of pro-drugs to prevent degradation and enhance absorption is another bioavailability-enhancing expedient which has been reported in the literature. EPO Publication 036534 reports hydroxyaryl or hydroxyaralkyl acid or salts, amides or esters of beta-lactam antibiotics as having increasing oral absorption. U.S. Pat. No. 4,673,534 reports sulfonic salts of carnitine have enhanced bioavailability. EPO Publication 090344 reports the use of 1,3-dioxolen-2-one derivates of drugs such as ampicillin provides greater bioavailability. EPO Publication 070013 reports the use of (5-R-2-oxo-1,3-dioxolen-4yl)methyl derivates of drugs such as antibiotics have enhanced bioavailability. U.S. Pat. No. 4,440,740 reports the use of alpha-keto aldehydes as enhancing gastro-intestinal drug absorption of numerous drugs. U.S. Pat. No. 4,443,435 reports the use of prodrugs of 6-mercaptopurine and related drugs for enhanced bioavailability. U.S. Pat. No. 4,694,006 reports acyl- or acyloxymethyl-allopurinol prodrugs having enhanced bioavailability. U.S. Pat. No. 4,747,062 reports the use of substituted benzoate ester prodrugs of betaestradiol and ethynyl estradiol for improved bioavailability. U.S. Pat. No. 4,771,073 reports the formation of L-dopa ester prodrugs to enhance bioavailability. U.S. Pat. Nos. 3,888,848 and 3,996,236 report penicillin prodrugs as having enhanced bioavailability. U.S. Pat. No. 4,021,546 report prodrug forms of digoxin having enhanced bioavailability. U.S. Pat. No. 4,058,621 reports the use of iron salts to enhance bioavailability of iron. U.S. Pat. No. 4,201,866 reports o-hemi-succinate of propanolol as a prodrug having enhanced bioavailability. U.S. Pat. No. 4,407,795 reports an inclusion compound of p-hexadecylamino benzoic acid sodium salt in beta-cyclodextrin which provides enhanced bioavailability. U.S. Pat. No. 4,722,928 describes n-oxide prodrugs of 3-hydroxy morphinans as having enhanced bioavailability. U.S. Pat. No. 4,268,441 describes prodrug forms of ketosteroidal sex hormones as having increased bioavailability.

Vasodilators have been used in combination with other drugs. In EPO Publication 106335, the use of a coronary vasodilator, diltiazem, is reported to increase oral bioavailability of drugs which have an absolute bioavailability of not more than 20%, such as adrenergic beta-blocking agents (e.g., propranolol), catecholamines (e.g., dopamine), benzodiazepine derivatives (e.g., diazepam), vasodilators (e.g., isosorbide dinitrate, nitroglycerin or amyl nitrite), cardiotonics or antidiabetic agents, bronchodilators (e.g., tetrahydroisoquinoline), hemostatics (e.g., carbazochrome sulfonic acid), antispasmodics (e.g., timepidium halide) and antitussives (e.g., tipepidine). Diltiazem has not been reported to be a gastrointestinal vasodilator. No mechanism of action is provided, and thus there is no basis for extrapolation from this disclosure that other vasodilators will act to increase bioavailability.

L. Ther and D. Winne (1971), *Drug Absorption*, pp. 57–69, discuss the dependence of intestinal drug absorption on blood flow. A complex relationship is described. Blood flow in the stomach and intestine is suggested as a factor in determining drug bioavailability by D.E. Cadwallader, (1971) *Biopharmaceutics and Drug Interactions*, (Roche Laboratories, Nutley, NJ) p. 53. At page 108 of this publication it is suggested that reserpine and quanethidine could increase the rate of absorption of orally administered drugs by increasing the blood flow to the GI tract. No experimental results were provided showing this to be the case.

A. J. McLean, et al. (1978), "Food, splanchnic blood flow, and bioavailability of drugs subject to first-pass metabolism," *Clin. Pharmacol. Ther.* 24:5–10, attempt to explain, via computer modeling, increased bioavailability of drugs such as propranolol or metoprolol after a meal. They predict that since not only food, but also drugs, enhance splanchic blood flow, the vasodilator hydralazine should enhance the bioavailability of propranolol or similar drugs which require metabolism through the liver to be effective. This prediction is borne out in D.W. Schneck and J.E. Vary (1984), "Mechanism by which hydralazine increases propranolol bioavailability," *Clin. Pharmacol. Ther.* 35:447–453, where the authors conclude that the increased bioavailability is due to hemodynamic effects. There is no disclosure or suggestion in these references that gastrointestinal vasodilators enhance bioavailability of drugs which enter the bloodstream in active form by passive diffusion.

Nicotinic acid (niacin) is a known vasodilator which causes hyperemia in many parts of the body, including the mucous membrane of the stomach. See L. Condorelli (1964), "Nicotinic Acid in the Therapy of the Cardiovascular Apparatus," *Niacin in Vascular Disorders and Hvoeremia*, R. Altschul (ed.), pp. 162–164. However, its effects on bioavailability have not previously been reported. Nicotinic acid is a component of Card-Colaldon ® (Hoechst Corporation), which contains 0.125 mg digoxin, 400 mg pentifylline and 100 mg of nicotinic acid. This formulation is provided in a sustained-release tablet containing the nicotinic acid and pentifylline in the core, with the digoxin coated onto the tablet core. Nicotinic acid in high doses (3–6 g/day), has been used as a cardiovascular drug. See Svedmyr, N. et al. (1970), "Dose-response relationship between concentration of free nicotinic acid concentration of plasma and some metabolic and circulatory effects after administration of nicotinic acid and pentaerythritol tetranicotinate in man," in *Metabolic Effects of Nicotinic Acid and its Derivatives*, Gey, K.F and Carlson, L.A. (eds.), Hans Huber Publishers, pp. 1085–1098). It increases stroke volume of the heart, decreases peripheral vascular resistance and lowers low density lipids and cholesterol in the blood. As nicotinic acid is present in the Card-Cosaldon ® formulation in the core of the tablet where it becomes available only after the digoxin has been solubilized, it is evident this component was not included in the formulation as a bioavailability enhancer.

The bioavailability of digoxin in the Card-Cosaldon ® formulation has been studied in H.-G. Grigoleit et al. (1976) "Untersuchung zur Bioverfugbarkeit von Digoxin aus Card-Cosaldon ® and alkoholischer Digoxinlosung als Standard im intraindividuellen Vergleich" ["Within-Patient Comparison Study on the Bioavailability of Digoxin from Card-Cosaldon ® and from an Alcoholic Digoxin Solution as a Standard"] *Therapiewoche* 26:5722–5729. This study reports that the digoxin in the tablet preparation had the same bioavailability as in an alcoholic solution of digoxin alone. There is no suggestion in this article that nicotinic acid is a bioavailability enhancer, nor is any mechanism postulated to explain the bioavailability of digoxin in the tablet formulation.

Nicotinic acid has been tested in combination with sodium bicarbonate to make an effervescing tablet. N.-O Lindberg (1970), "Preparation of effervescent tablets containing nicotinic acid and sodium bicarbonate," *Acta Pharm. Svecica* 7:23–28. This article neither discloses nor suggests the use of nicotinic acid as a bioavailability enhancer for drugs, nor a combination of nicotinic acid with drugs which must be absorbed into the bloodstream to be active.

In 1985, A.R. Waller et al., in "Bioavailability Studies of Etofibrate in Rhesus Monkeys," *Arnzeim.-Forsch./Drug Res.* 35:489–492 reported that the rates and extent of bioavailability of nicotinic acid or clofibric acid administered as a mixture were similar to those of these drugs administered alone. Thus, neither drug affected the absorption of the other in rhesus monkeys. Since the mechanism of absorption of clofibric acid is not known, this article would lead me away from pursuing the line of inquiry which led to this invention.

Nicotinic acid (niacin) is present in commercial vitamin preparations in the form of niacinamides such as niacinamide ascorbate. In the niacinamide form it does not cause the vasodilation or flushing which may be experienced as a side effect to the administration of nicotinic acid per se. Nicotinic acid is a water-soluble B vitamin which is considered relatively harmless even at high dosages. See, e.g., L. R. Mosher (1970), "Nicotinic Acid Side Effects and Toxicity: A Review," *Amer. J. Psychiat.* 126:1290–1297. It increases peripheral blood flow. See, e.g., D.I. Abramson, et al. (1940), "Effect of Nicotinic Acid on Peripheral Blood Flow in Man," Am. J. Med. Sci. 200:96–102; R.J. Popkin (1939), "Nicotinic Acid, Its Action on the Peripheral Vascular System," Am. Heart J. 18:697–704. It increases heart rate and cardiac output, but has only minor effects on blood pressure, along with being useful in the treatment of a number of other conditions. L. Condorelli (1964) "Nicotinic Acid in the Therapy of The Cardiovascular Apparatus," *Niacin in Vascular Disorders and Hyperemia*, R. Altschul (ed.), pp. 156–207.

Surprisingly, although the flushing effect of nicotinic acid has been found to be reduced by the administration of acetylsalicylic acid (R.G.G. Andersson, et al. (1977), "Studies on the Mechanism of Flush Induced by Nicotinic Acid," Acta Pharmacol. et Toxicol. 41:1–10), the bioavailability of aspirin was found in the present invention to be enhanced by administration of nicotinic acid therewith. The flushing effect occurs only while the nicotinic acid plasma concentration is increasing, and disappears when the concentration reaches a constant level, however the vasodilation effect continues after the flushing has subsided. N. Svedmyr, et al. (1969), "The relationship between the plasma concentration of free nicotinic acid and some of its pharmacologic effects in man," Clin. Pharmacol. Therapeut. 10:559–570. Absorption of nicotinic acid is not affected by food ingestion. H. Bechgaard and S. Jespersen (1977), "GI Absorption of Niacin in Humans," J. Pharmaceut. Sci. 66:871–872.

Many other vasodilators are known to the art, and have been used therapeutically by themselves, i.e., not in combination with other drugs. See, e.g., M. Nickerson, (1975) "Vasodilator Drugs" in *The Pharmacological Basis of Therapeutics*, Chapter 34, pp. 745–760.

Bioavailabilities of drugs suitable for use in the preferred embodiments of this invention have been studied, however, not in connection with increasing bioavailability through the use of vasodilators affecting the GI tract. Some articles discussing the bioavailability of painkillers are: V. J. Stella et al. (February 1978), "Current Drug Bioavailability Information, Acetaminophen and Aspirin," Kans Pharmacy, pp. 12–13; and G. Levy et al. (1963), "Biopharmaceutical Aspects of the Gastrointestinal Absorption of Salicylates," *Salicylates, An International Symposium*, Dixon et al. (eds.), pp. 9–17. Articles discussing the bioavailability of theophylline are: R. Koysooko et al. (1974), "Relationship between theophylline concentration in plasma and saliva of man," Clin. Pharmacol. Therapeut. 15:454–460; G. Levy, et al. (1974), "Indirect Plasma-Theophylline Monitoring in Asthmatic Children by Determination of Theophylline Concentration in Saliva," Pediatrics 53:873–876; L. Hendeles et al. (1985), "Update on the Pharmacodynamics and Pharmacokinetics of Theophylline," CHEST 88:103S-111S; and K. M. Piafsky and R. I. Ogilvie (1975), "Dosage of Theophylline in Bronchial Asthma," New Engl. J. Med. 292:1218–1222.

It is apparent from the foregoing discussion that although vasodilators affecting the gastrointestinal tract, such as nicotinic acid, have been used alone or as components of pharmaceutical preparations for administration to patients, there has been no recognition in the art that in a formulation designed for rapid release and absorption into the bloodstream of drugs through the gastrointestinal tract via passive diffusion, such vasodilators, e.g., nicotinic acid, act to enhance the bioavailability of other drugs.

SUMMARY OF THE INVENTION

This invention provides a pharmaceutical composition in oral dosage form designed for rapid release and absorption of a pharmaceutically active compound into the bloodstream, comprising a combination of: (1) a therapeutically effective amount of a pharmaceutically active compound, which compound enters the bloodstream by passive diffusion through the GI tract; and (2) a vasodilator which affects the blood vessels of the GI tract in an amount sufficient to enhance the bioavailability of said pharmaceutically active compound. The pharmaceutically active compound must be one which acts through being absorbed into the bloodstream through the gastrointestinal tract.

A method of increasing the bioavailability of pharmaceutically active compounds comprising administering them with an effective amount of said vasodilator is also provided.

The most preferred embodiment of this invention comprises theophylline as the pharmaceutically active compound and nicotinic acid (niacin) as the vasodilator. Other preferred embodiments include combinations of nicotinic acid with painkillers such as aspirin, ibuprofen and acetaminophen. Further embodiments include combinations of nicotinic acid with phenytoin, verapamil and antihistamines. Other pharmaceutically active compounds known to the art which are suitable for use in acute situations requiring rapid achievement of minimum effective concentrations in the blood are also suitable for use in this invention. Other vasodilators which increase the blood flow to the GI tract as known to the art, such as reserpine, may also be used, as may precursor compounds such as pentaerythritoltetranicotinate (Niceritrol) which hydrolizes to nicotinic acid in the stomach. R. Brattsand and L. Harthon (1975), "Plasma Levels of Nicotinic Acid Compounds in Niceritrol-Treated Rabbits," Acta Pharmacol. Toxicol. 36:203–214.

In a preferred embodiment, the vasodilator, preferably nicotinic acid, comprises a layer around a core of the pharmaceutically active compound in an oral dosage preparation.

In a second preferred embodiment, the vasodilator is present in a homogenous mixture with a pharmacologically active compound, for example, in a tablet or in thin gelatin encapsulation.

BRIEF DESCRIPTION OF THE FIGURES

FIG. 1 is a graph showing theophylline blood levels as a function of time after administration, comparing theophylline in combination with nicotinic acid with theophylline alone.

DETAILED DESCRIPTION OF THE PREFERRED EMBODIMENTS

The combination of a pharmaceutically active compound with a GI tract vasodilator of this invention must be administered in oral dosage form. Oral dosage forms such as tablets, pills, powders, granules, liquid dosage forms such as solutions, syrups, emulsions, elixirs, suspensions and other oral dosage forms known to the art may be used provided such dosage forms are designed for rapid or immediate release, e.g., by rapid disintegration, and absorption into the bloodstream rather than being designed for sustained release. In a preferred embodiment, the pharmaceutically active compound is present in the core of a tablet, surrounded by a layer of the vasodilator so that vasodilation is occurring when the active compound begins to dissolve.

The pharmaceutically active compound whose bioavailability is enhanced may be any compound which is ingested in its active form and enters the bloodstream in active form through the gastrointestinal tract via passive diffusion. This invention is especially suited to drugs administered in acute situations where rapid achievement of effective levels in the bloodstream are required. Preferred drugs of this type include bronchodilators such as theophylline; aspirin; non-steroidal anti-inflammatory drugs such as ibuprofen; non-aspirin analgesic antipyretics such as acetaminophen; phenytoin; verapamil; and antihistamines such as chlorpheniramine.

In some circumstances it may be desirable to achieve rapid effective blood levels of drugs usually administered in sustained release form, such as blood pressure drugs or decongestant/antihistamine combinations, however, compositions containing such drugs comprise less preferred embodiments of this invention.

The pharmaceutically active compound may be one which enters the bloodstream in its active form or one which is converted to active form by mechanisms within the body after it has entered the bloodstream. It may also be converted to active form within the GI tract. Drugs which require "first pass metabolism," or passage through the liver to be converted to active form are excluded. Also, drugs such as decongestants which produce vasoconstriction as a necessary part of their mechanism of therapeutic action are excluded from the scope of this invention.

Therapeutically effective amounts of the active pharmaceuticals whose bioavailabilities are enhanced by the methods of this invention are known to the art. Therapeutically effective amounts are amounts providing appropriate levels of the active compound in the bloodstream. Because of the increase in bioavailability of the drug by this invention, smaller than normal dosages may be required to reach therapeutically effective levels, all as may be readily determined without undue experimentation by those skilled in the art. The term "therapeutically effective amounts" encompasses blood levels between the minimum effective concentration of the drug and amounts at which toxicity or other undesirable reactions occur.

Dosages for the pharmaceutically active compound can be readily ascertained by those skilled in the art, and range from minimum effective amounts to amounts causing toxicity or undesirable side effects which outweigh the beneficial effects of the drugs. The nicotinic acid may be used in any effective amount. As is known to the art, high dosages up to 6 grams per day of nicotinic acid are tolerated. It may be desirable to minimize the flushing effect which occurs at about 100 mg –150 mg. However, some flushing effect may be deliberately induced to enhance the placebo effect of the composition. In the preferred embodiment of this invention, using theophylline as the active pharmaceutical and nicotinic acid as the bioavailability enhancer, the preferred dosage of theophylline is between about 100 mg and about 450 mg, and of nicotinic acid is between about 10 mg and about 100 mg, and more preferably between about 20 mg and about 100 mg. When aspirin and nicotinic acid are used, the preferred dosage of aspirin is between about 80 mg and about 650 mg, and the preferred dosage of nicotinic acid is between about 10 mg and about 100 mg. When acetaminophen and nicotinic acid are used, the preferred dosage of acetaminophen is between about 80 mg and about 500 mg, and the preferred dosage of nicotinic acid is between about 0 mg and about 100 mg. When phenytoin and nicotinic acid are used, the preferred dosage of phenytoin is between about 30 mg and about 100 mg, and the preferred dosage of nicotinic acid is between about 10 mg and about 100 mg. When verapamil and nicotinic acid are used, the preferred dosage of verapamil is between about 40 mg and about 120 mg, and the preferred dosage of nicotinic acid is between about 10 mg and about 100 mg.

The pharmaceuticals useful in this invention are those which enter the bloodstream via passive diffusion (also called passive transfer) through the gastrointestinal tract. Passive diffusion is discussed in Cadwallader, D.E. (1971), *Biopharmaceutics and Drug Interactions*, p. 48. In passive diffusion, the cell membranes of the gastrointestinal tract play a passive role and do not actively participate in the transport process. The passive diffusion process follows first-order kinetics, and under normal conditions, the transfer rate is proportional to the concentration of the drug in the GI tract. This rate is enhanced by the methods of this invention through vasodilation of the blood vessels in the GI tract.

Vasodilators which affect the blood vessels of the GI tract are known to the art and include nicotinic acid (niacin), nicotinyl alcohol which oxidizes to nicotinic acid, pentaerythritoltetra nicotinate, which hydrolyzes to nicotinic acid in the stomach, and reserpine. Vasodilators are discussed in Nickerson, M. (1975), "Vasodilator Drugs," in *The Pharmacological Basis of Therapeutics*, Goodman, L.S. and Gilman, A. (eds.), pp. 727–743. Preferably, the vasodilator and dosage used are selected so as to minimize effect on blood pressure or heart rate. Nicotinic acid is preferred for its minimal effects on blood pressure and heart rate and for its lack of toxicity in the recommended dosage ranges. Nicotinic acid is also preferred because it is a vitamin required by the body. For acute situations such as asthmatic attacks, where rapid relief is essential, dosages of nicotinic acid are preferably about 100 mg. Preferred dosage ranges for use in less acute situations are those which enhance bioavailability without causing excessive flushing reactions, such as between about 10 mg and about 50 mg. When other vasodilators such as reserpine are used, dosages up to but not including toxic levels as known to the art may be used in acute situations, however lesser effective dosages are preferred. Those skilled in the art are able to determine such effective dosages by methods well known to the art. Any vasodilator known to the art to increase circulation to the GI mucosa may be used, so long as adverse interactions which occur between the vasodilator and the drug whose bioavailability is desired to be enhanced are minimal. Such interactions are readily ascertained by known methods without undue experimentation.

Bioavailability includes the following factors: rate (or time after administration) of achievement of minimum effective drug serum concentration, maximum drug serum concentration, rate (or time after administration) of achievement of maximum drug serum concentration, and the area under the drug serum concentration-time curve above a line representing minimum effective drug serum concentration. Enhancement of bioavailability means an increase in any one or more of these factors.

In the method for enhancing bioavailability of a pharmaceutically active compound by administering same in combination with a vasodilator, it is preferred that the pharmaceutically active compound be formulated with the vasodilator in a single dosage form such as a tablet, capsule, or the like, as above described, however, the two components may also be administered separately at approximately the same time. In the latter case it is preferred that the vasodilator be administered first and that the pharmaceutically active compound be administered no more than about 15 minutes thereafter. The preferred method of this invention utilizes the preferred compositions of this invention.

The following examples are provided by way of illustration, and are not intended to limit the scope of this invention which is effective when practiced with any of the above-described classes of pharmaceutically active compounds and vasodilators. Modification of dosage forms and amounts may be accomplished without undue experimentation based on the teachings of the foregoing description and the following examples.

EXAMPLES

Example 1:

Nicotinic Acid and Theophylline

Three 100 mg. tablets of Slophyllin (Trademark of A. H. Rorer Company, Ft. Washington, PA, a theophylline preparation designed for immediate release, from a new bottle were mixed with one 100 mg. niacin tablet from a new bottle in a mortar and pestle. The contents were placed in an empty gelatin capsule and ingested by a human patient immediately after the first blood draw. Controls were done several days later using the same patient, with the same amount of Slophyllin without nicotinic acid using the same procedures. The results shown in Table 1 demonstrate that the blood levels for theophylline reached an effective therapeutic level of 7.4 μg/ml effective for symptom relief within one-half hour, and reached peak levels (within safe blood levels) of 8.2 μg/ml within an hour-and-a-half, retaining therapeutic blood levels of over 7.0 μg/ml for the duration of the test (four hours).

TABLE 1

| | TIME AFTER ADMINISTRATION (HR:MIN) | | | | | | | |
|---|---|---|---|---|---|---|---|---|
| | 0 | :33 | 1:04 | 1:32 | 2:01 | 2:36 | 3:02 | 4:00 |
| Theophylline plus nicotinic acid (Blood levels μg/ml) | <0.5 | 7.4 | 7.5 | 8.2 | 7.8 | 7.3 | 7.7 | 7.3 |

| | TIME AFTER ADMINISTRATION (HR:MIN) | | | | | | |
|---|---|---|---|---|---|---|---|
| | 0 | :29 | 1:03 | 1:33 | 2:01 | 2:30 | 3:04 |
| Theophylline (Blood levels μg/ml) | <.05 | <0.5 | 2.2 | 4.4 | 5.3 | 7.0 | 7.2 |

Controls showed a two and one-half hour period to reach effective blood levels reached with the combination drug in one-half hour.

Example 2:

Reserpine and Acetylsalicylic Acid

Three beagles were given reserpine orally in slurry in dose of 0.125 mg per day for five days. On the sixth day, acetylsalicylic acid (ASA) 5 grains po was administered in slurry and plasma salicylic acid (SA) concentrations were determined. This test was repeated two weeks later with the exclusion of reserpine pretreatment. Results are shown in Table 2.

TABLE 2

| | Reserpine Pretreated Dogs | Non-Treated Dogs |
|---|---|---|
| % of Dose of ASA Absorbed (using IV ASA as 100% absorption) | 99% | 87.5% |
| % of maximum concentration at t = | | |
| 10 minutes | 48% | 24% |
| 20 minutes | 72% | 47% |
| 30 minutes | 81% | 70% |
| 2 hours | 100% | 100% |
| Comparison to plasma SA in humans following 5 grains per os (averages for 10 male adult volunteers) | | |
| t =  Human | | |
| 10 minutes  2.56 μg/ml | 42.3 μg/ml | 19.9 μg/ml |
| 60 minutes  16.25 μg/ml | 80.1 μg/ml | 72.8 μg/ml |
| 2 hours  16.76 μg/ml | 88.9 μg/ml | (max) 81.4 μg/ml |

Plasma concentration of SA was considerably higher at each time interval in reserpine-treated dogs, the greatest differences occurring in the early stages of the absorption phase. Peak plasma concentrations of SA occurred at the same time in both tests. Following the first hour, both curves were similar, almost superimposable, and elimination kinetics were similar. Total area under the plasma level curve was 13.2% higher in the reserpine-treated dogs at 8 hours than in the non-pretreated dogs. This compares favorably to a 14.5% higher total AUC after IV dosing of 5 grains ASA into beagle femoral vein, and appears to indicate near-complete absorption induced by reserpine.

As with theophylline, we see a "spike" effect when a vasodilator is present during the first few minutes after dosing, then absorption assumes a normal profile.

Example 3

Nicotinic Acid and Acetylsalicylic Acid

One 325 mg aspirin tablet was triturated with one 100 mg nicotinic acid tablet in mortar and pestle, encapsulated and administered to a human being by mouth. Venous blood samples were taken at time intervals listed below. The next day, one 325 mg aspirin tablet was triturated in mortar and pestle and encapsulated. After administration to the human volunteer, blood samples were taken at the same time intervals as the previous test. Relative salicylic acid concentrations of the samples were compared using fluorescence units as determined by spectrofluorometer. Results are set forth in Table 3. These results show that within 15 minutes, nicotinic acid increases the aspirin blood levels by 28% over aspirin alone, and after one hour by 170%.

TABLE 3

| | Time After Administration (Min.) | | | | |
|---|---|---|---|---|---|
| | 0 | 15 | 30 | 45 | 60 |
| Aspirin plus nicotinic acid (Fluor. units) | .002 | .115 | .282 | .349 | .776 |
| Aspirin (Flour. units) | .010 | .090 | .145 | .230 | .288 |

I claim:

1. A pharmaceutical composition in oral dosage form designed for rapid release and absorption into a bloodstream, comprising a combination of a therapeutically effective amount of theophylline and nicotine acid in an amount sufficient to enhance the bioavailability of said theophylline.

2. A method of increasing the bioavailability of theophylline administered in its active form, comprising orally administering a pharmaceutically-effective amount of said theophylline, and nicotine acid in a form designed for rapid dissolution of said theophylline and nicotine acid and absorption into the bloodstream, wherein said nicotinic acid is present in an amount sufficient to enhance to bioavailability of said theophylline.

* * * * *